United States Patent [19]

Sandri et al.

[11] 4,340,743

[45] Jul. 20, 1982

[54] DERIVATIVES OF MONO-(ALKYLENE UREIDO ALKYL) UREAS, AND BIS-(ALKYLENE UREIDO ALKYL) UREAS

[75] Inventors: Joseph M. Sandri, Arnold; John W. Calentine, Pasadena; Seymour M. Linder; Yves J. Billioux, both of Baltimore, all of Md.

[73] Assignee: Alcolac Inc., Baltimore, Md.

[21] Appl. No.: 163,488

[22] Filed: Jun. 27, 1980

Related U.S. Application Data

[63] Continuation-in-part of Ser. No. 157,238, Jun. 6, 1980.

[51] Int. Cl.³ .......................................... C07D 233/36
[52] U.S. Cl. .................................. 548/318; 544/296; 544/316; 548/319; 548/320
[58] Field of Search ..................... 548/318, 319, 320; 544/296, 316

[56] References Cited

U.S. PATENT DOCUMENTS

| | | | |
|---|---|---|---|
| 2,613,212 | 10/1952 | Hurwitz et al. | 548/318 |
| 2,694,695 | 1/1955 | Bortnick | 526/302 |
| 2,727,016 | 12/1955 | Hankins et al. | 526/263 |
| 2,828,224 | 3/1958 | Alps et al. | 428/473 |
| 2,831,833 | 4/1958 | Aycock et al. | 525/336 |
| 2,832,756 | 4/1958 | Melamed | 526/218 |
| 2,837,499 | 5/1958 | Melamed | 526/218 |
| 2,840,545 | 5/1958 | Yost | 526/263 |
| 2,871,223 | 1/1959 | Hankins et al. | 525/336 |
| 2,881,155 | 4/1959 | Hankins | 526/263 |
| 2,883,304 | 4/1959 | Kine et al. | 428/240 |
| 2,980,652 | 4/1961 | Melamed et al. | 526/262 |
| 3,014,042 | 12/1961 | Mantz | 548/320 |
| 3,350,363 | 10/1967 | Hurwitz | 526/263 |
| 3,356,627 | 12/1967 | Scott | 260/29.6 RB |
| 3,356,654 | 12/1967 | Sekmakas | 526/258 |
| 3,356,655 | 12/1967 | Sekmakas | 525/328 |
| 3,509,085 | 4/1970 | Sekmakas | 260/29.6 R |
| 4,104,220 | 8/1978 | Sims | 260/29.6 R |
| 4,111,877 | 9/1978 | Dixon et al. | 260/29.6 R |
| 4,151,142 | 4/1979 | Herman et al. | 260/29.6 R |

OTHER PUBLICATIONS

Parker, R., et al., *Chem. Rev.*, 59, 741 (1959).
*Chemical Abstracts*, 81:121,360y (1974), [Porret et al., German Ols. 2,342,432, 3/7/74].

*Primary Examiner*—Richard A. Schwartz
*Attorney, Agent, or Firm*—Finnegan, Henderson, Farabow, Garrett & Dunner

[57] ABSTRACT

The invention provides new compounds which are cyclic alkylene ureas produced by the reaction of an alkylene urea selected from the group consisting of a mono-(alkylene ureido alkyl) urea, a bis-(alkylene ureido alkyl) urea, and mixtures thereof, with an unsaturated glycidyl ether or ester, such as allyl glycidyl ether. The new compounds are monomers which may be incorporated in aqueous emulsion polymer systems and are useful as wet adhesion promoters for latex paints.

17 Claims, No Drawings

DERIVATIVES OF MONO-(ALKYLENE UREIDO ALKYL) UREAS, AND BIS-(ALKYLENE UREIDO ALKYL) UREAS

This application is a continuation-in-part of the application of the inventors herein entitled "Derivatives of Aminoalkyl Alkylene Ureas And Their Use As Wet Adhesion Promoters," Ser. No. 157,238, filed on June 6, 1980. The disclosure of said application Ser. No. 157,238 is hereby expressly incorporated by reference, in its entirety, herein.

FIELD OF THE INVENTION

This invention relates to new chemical compounds, compositions, and their preparation and use. More particularly, this invention relates to the preparation of certain polymerizable alkylene ureas which are especially useful as monomers for latex paint compositions to promote wet adhesion of such paint compositions.

BACKGROUND OF THE INVENTION

The use of water-based emulsion polymer systems as protective and decorative coatings for many types of surfaces has become widespread. The so-called latex paint is commonly used by individuals in homes and industrially. While oil-based systems are known to retain their adhesive properties under wet or humid conditions, a characteristic called "wet adhesion," the tendency of many water-based coatings to lose their adhesive properties when wet has limited the usefulness of such coatings. This is particularly true for paints based on vinyl-acrylic or allacrylic latexes which otherwise are attractive as paint vehicles.

Paints intended for outdoor use are frequently exposed to moisture and humidity, as are paints used on interior surfaces in wet or humid atmospheres, such as in bathrooms and kitchens. Good wet adhesion is an important attribute of paints applied to those surfaces and others where resistance to water and abrasion is important, as where paints are exposed to washing or scrubbing, and where water-based paints are applied to glossy surfaces. In these situations, the need for improved wet adhesion of aqueous emulsion polymer systems is particularly great.

The art has recognized the problem of loss of adhesive properties in latex paints when wet, and a variety of additives to latex systems to improve wet adhesion has been proposed. For example, U.S. Pat. No. 3,356,655, issued on Dec. 5, 1967, and U.S. Pat. No. 3,509,085, issued on Apr. 28, 1970, disclose a number of ethylenically unsaturated hydroxy-functional amines which are said to be useful in improving adhesion and water resistance of latex paints. In addition, U.S. Pat. No. 4,111,877, issued on Sept. 5, 1978, discloses certain imidazolidinone derivatives which are said to improve the adhesive properties of latex paint.

It has now been found that latex-containing surface coatings and coating compositions having excellent wet adhesion properties can be produced by including in the monomer system one or a mixture of novel polymerizable cyclic alkylene ureas having ureido, hydroxyl and allylic functionalities. In particular, the new compounds of this invention have been found to be especially useful in water-based latex-containing paints and can also be employed as comonomers in solution polymers.

SUMMARY OF THE INVENTION

In related application Ser. No. 157,238, referred to above, there are disclosed new polymerizable cyclic alkylene ureas having hydroxyl and amine functionalities and which are produced by the reaction of an omega-amino alkyl or substituted alkyl alkylene urea with an unsaturated glycidyl ether or ester. The compounds disclosed in said application have the generic formula:

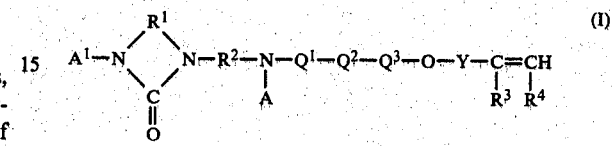

where $R^1$ is alkylene having 2 to 3 carbon atoms, and preferably $R^1$ is $C_2H_4$;

$R^2$ is alkylene having 2 to about 10, preferably 2 to 4, carbon atoms, and most preferably, $R^2$ is $C_2H_4$;

$R^3$ is H or $CH_3$, preferably H;

$R^4$ is H or $CH_3$ and may be the same as or different from $R^3$, and preferably $R^4$ is H;

$Q^1$ is $(R^5\text{-}O)_m$ where m is zero or an integer from 1 to about 100, preferably zero or 1 to about 75, and most preferably zero, and $R^5$ is a linear or branched alkylene, alkoxyalkylene, cycloalkylene, cycloalkoxyalkylene, arylalkylene or aryloxyalkylene residue having 2 to about 20, preferably 2 to 6, carbon atoms;

$Q^2$ is

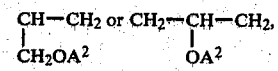

where $A^2$ is H or

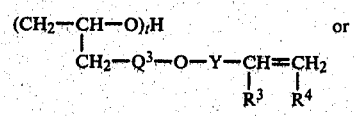

wherein t is zero or an integer from 1 to 10, preferably $Q^2$ is

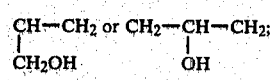

$Q^3$ is $(O\text{-}R^6)_n$ where n is zero or an integer from 1 to about 100, preferably zero or from 1 to about 75, and most preferably n is zero, and may be the same as or different from m, and $R^6$ is a linear or branched alkylene, alkoxyalkylene, cycloalkylene, cycloalkoxyalkylene, arylalkylene or aryloxyalkylene residue having 2 to about 20, preferably 2 to 6, carbon atoms, and may be the same as or different from $R^5$;

Y is $CH_2$ or

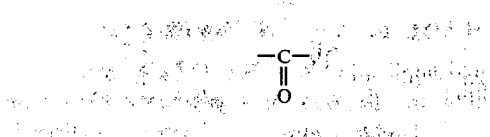

preferably CH$_2$;

A is H, Q$^4$H or

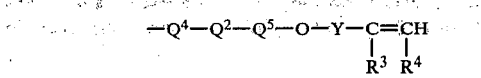

where Q$^4$ is (R$^7$-O)$_p$ where p is zero or an integer from 1 to about 100, preferably 1 to about 75, and may be the same as or different from m and n and preferably is the same as m; and R$^7$ is a linear or branched alkylene, alkoxyalkylene, cycloalkylene, cycloalkoxyalkylene, arylalkylene, or aryloxyalkylene residue having 2 to about 20, preferably 2 to 6, carbon atoms, and may be the same as or different from R$^5$ and R$^6$ and preferably is the same as R$^5$;

Q$^5$ is (O-R$^8$)$_q$ where q is zero or an integer from 1 to about 100, preferably 1 to about 75, and may be the same as or different from m, n and p, and preferably is the same as n, and R$^8$ is a linear or branched alkylene, alkoxyalkylene, cycloalkylene, cycloalkoxyalkylene, arylalkylene or aryloxyalkylene residue having 2 to about 20, preferably 2 to 6, carbon atoms, and may be the same as or different from R$^5$, R$^6$ and R$^7$, and preferably is the same as R$^6$; and Q$^2$, Y, R$^3$ and R$^4$ are as defined above; and A$^1$ is H, Q$^6$H;

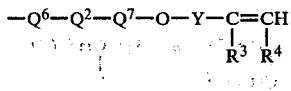

or A where Q$^6$ is (R$^9$-O)$_r$ where r is zero or an integer from 1 to about 100, preferably 1 to about 75, and may be the same as or different from m, n, p and q and preferably is the same as m, and R$^9$ is a linear or branched alkylene, alkoxyalkylene, cycloalkylene, cycloalkoxyalkylene, arylalkylene or aryloxyalkylene residue having 2 to about 20, preferably 2 to 6, carbon atoms, and may be the same as or different from R$^5$, R$^6$, R$^7$ and R$^8$, and preferably is the same as R$^5$;

Q$^7$ is (O-R$^{10}$)$_s$ where s is zero or an integer from 1 to about 100, preferably 1 to about 75, and may be the same as or different from m, n, p, q and r, and preferably is the same as n, and R$^{10}$ is a linear or branched alkylene, alkoxyalkylene, cycloalkylene, cycloalkoxyalkylene, arylalkylene or aryloxyalkylene residue having 2 to about 20, preferably 2 to 6, carbon atoms, and may be the same as or different from R$^5$, R$^6$, R$^7$, R$^8$ and R$^9$, and preferably is the same as R$^6$; and Q$^2$, Y, R$^3$, R$^4$, and A are as defined above.

In the preferred embodiments of the compounds disclosed in Ser. No. 157,238, m and n are zero, whereby the compounds have the formula:

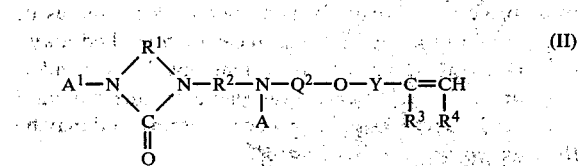

In the most preferred embodiments, R$^1$ is C$_2$H$_4$, R$^2$ is C$_2$H$_4$, A is either H or

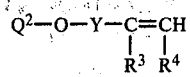

and A$^1$ is H whereby the compounds have the formula:

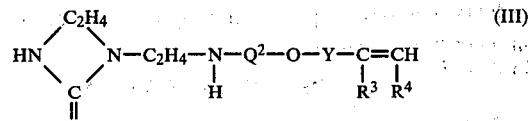

or the formula:

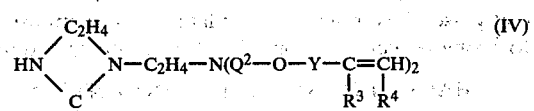

The compounds defined by formulae III and IV are aminoethyl imidazolidinones which contain hydroxyl functionality on the Q$^2$ moiety.

As disclosed in related application Ser. No. 157,238, the compounds described above may be formed by reacting an omega-amino alkyl or substituted alkyl alkylene urea with an unsaturated glycidyl ether or ester. Suitable omega-amino alkylene ureas have the formula:

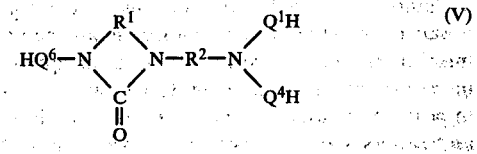

where R$^1$, R$^2$, Q$^1$, Q$^4$ and Q$^6$ are as defined above.

Preferably, the omega-amino alkylene ureas have the formula:

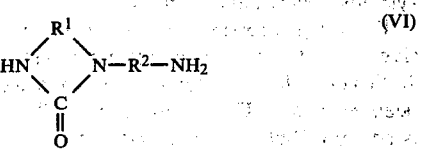

where R$^1$ and R$^2$ are as defined above. Most preferably, both R$^1$ and R$^2$ are C$_2$H$_4$, whereby the omega-amino alkylene urea is 2-amino-ethyl ethylene urea ("AEEU"), which is the compound having the formula:

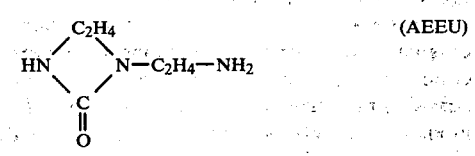

In accordance with the present invention, it has also been found that new cyclic alkylene ureas having hydroxyl and allylic functionalities, and useful in the manner disclosed in related application Ser. No. 157,238, can be produced by employing a urea selected from the group consisting of a mono-(alkylene ureido alkyl) urea, a bis-(alkylene ureido alkyl) urea and mixtures thereof in lieu of or in addition to the omega-amino alkyl alkylene ureas disclosed in said related application. For convenience, the mono-(alkylene ureido alkyl) ureas are at times referred to herein as "mono-urea" and the bis-(alkylene ureido alkyl) ureas referred to as "bis-urea".

The preferred reactants are bis-ureas, and the preferred bis-urea, corresponding to AEEU, is 1,3-bis-[2-(2-oxo-1-imidazolidinyl)-ethyl] urea ("bis-AEEU") which has the formula:

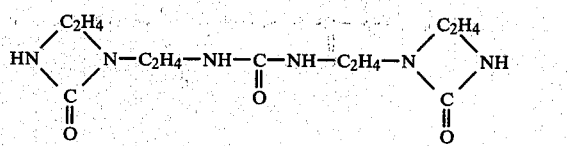
("BIS-AEEU")

In general, in accordance with the present invention, the bis-urea has the formula:

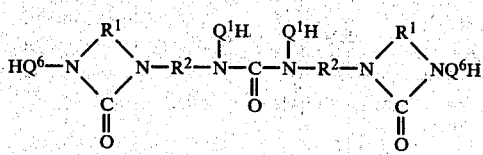
(BIS-V)

where $R^1$, $R^2$, $Q^1$ and $Q^6$ are as defined above.

It is preferred that the bis-urea have the formula:

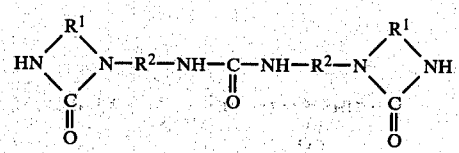
(BIS-VI)

Mono-ureas useful in accordance with the invention have the general formula:

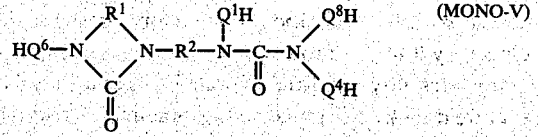
(MONO-V)

where $R^1$, $R^2$, $Q^1$, $Q^4$ and $Q^6$ are as defined above, and $Q^8$ is $(R^{11}$-O$)_w$ where w is zero or an integer from 1 to about 100, preferably 1 to about 75, and may be the same as or different from m, n, p, q, r and s, and preferably is the same as p, and $R^{11}$ is a linear or branched alkylene, alkoxyalkylene, cycloalkylene, cycloalkoxyalkylene, arylalkylene or aryloxyalkylene residue having 2 to about 20, preferably 2 to 6, carbon atoms, and may be the same as or different from $R^5$, $R^6$, $R^7$, $R^8$, $R^9$ and $R^{10}$, and preferably is the same as $R^7$. Preferably, the mono-ureas have the formula:

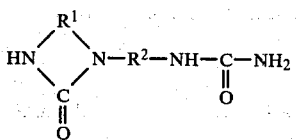
(MONO-VI)

Most preferably, both $R^1$ and $R^2$ both are $C_2H_4$.

The present invention also relates to compositions made by reacting a mono-urea or a bis-urea as described above, or mixtures thereof, alone or in admixture with omega-amino alkylene ureas having the formula V, with an unsaturated glycidyl ether or ester.

Suitable unsaturated glycidyl ethers and esters have the formula:

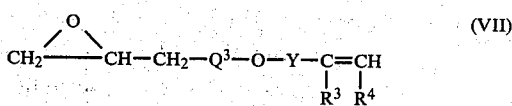
(VII)

where $Q^3$, Y, $R^3$ and $R^4$ are as defined above. Preferably, unsaturated glycidyl ethers are used having the formula:

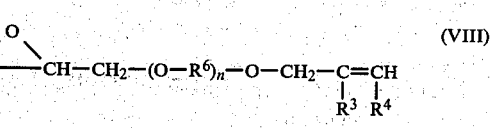
(VIII)

where $R^3$, $R^4$, $R^6$ and n are as defined above. It is preferred that $R^6$ is $C_2H_4$, and most preferably n is zero whereby the unsaturated glycidyl ether is:

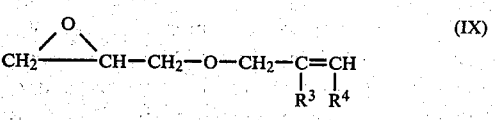
(IX)

where $R^3$ and $R^4$ are as defined above. It is within the scope of the invention to use mixtures of the alkylene ureas and/or the glycidyl compounds as reactants.

In another aspect, the invention relates to new polymerizable cyclic alkylene ureas derived from the reaction of a mono-urea, bis-urea or mixtures thereof with an unsaturated glycidyl ether or ester. Where a bis-urea is used, the polymerizable cyclic alkylene ureas have the general formula:

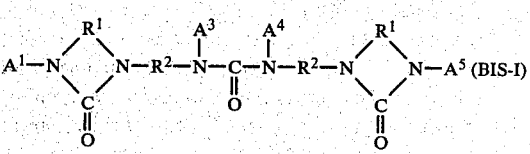
(BIS-I)

where $A^1$ and $A^5$ are each independently H, $Q^6$H or

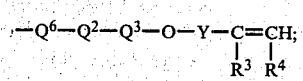

$A^3$ and $A^4$ are each independently H, $Q^1$H or $$-Q^1-Q^2-Q^3-O-Y-\underset{R^3}{\overset{|}{C}}=\underset{R^4}{\overset{|}{C}}H,$$

provided that at least one of $A^1$, $A^3$, $A^4$ and $A^5$ is a group containing the moiety $$-Q^2-Q^3-O-Y-\underset{R^3}{\overset{|}{C}}=\underset{R^4}{\overset{|}{C}}H;$$

and $R^1$, $R^2$, $R^3$, $R^4$, $Q^1$, $Q^2$, $Q^3$, $Q^6$ and Y are as defined above.

Where a mono-urea is used, the resultant polymerizable cyclic alkylene urea compounds of the present invention have the formula:

$$A^1-N\underset{\underset{O}{\overset{\|}{C}}}{\overset{R^1}{\diamond}}N-R^2-\underset{\overset{\|}{O}}{\overset{A^3}{\overset{|}{N}}}-C-N\overset{A^6}{\underset{A}{\diamond}} \quad \text{(MONO-I)}$$

where $R^1$, $R^2$, A, $A^1$ and $A^3$ are as defined above, and $A^6$ is H, $Q^8$H or $$-Q^8-Q^2-Q^3-O-Y-\underset{R^3}{\overset{|}{C}}=\underset{R^4}{\overset{|}{C}}H$$

where $Q^2$, $Q^3$, $Q^8$, Y, $R^3$ and $R^4$ are as defined above.

The compounds of the present invention may properly be called adducts of alkylene ureido alkyl ureas and unsaturated glycidyl ethers or esters. The compounds of this invention also are monomers capable of polymerization at their double bonds. Thus, the products of the reaction described above are useful as components of monomer systems, especially monomer systems used in forming aqueous emulsion polymers for coating surfaces. Accordingly, other aspects of the present invention include compositions comprising the monomers of the present invention, polymers made therefrom and compositions, especially acrylic and vinyl-acrylic latex paints comprising polymers made from the monomers of this invention. In addition, the present invention provides a method of enhancing the wet adhesion of aqueous polymer systems by incorporating the compounds of the present invention in the precursor monomer mixtures.

The general description of the invention above, along with the more detailed description of particular and preferred embodiments of the invention hereinafter, serve to illustrate the various aspects of this invention.

DETAILED DESCRIPTION OF PARTICULAR EMBODIMENTS

The monomers of the present invention may be derived from alkylene ureido alkyl ureas selected from the group consisting of mono-(alkylene ureido alkyl)ureas, bis-(alkylene ureido alkyl)ureas, and mixtures thereof, having the formula;

$$HQ^6-N\underset{\underset{O}{\overset{\|}{C}}}{\overset{R^1}{\diamond}}N-Z$$

where Z is $$R^2-\underset{\overset{\|}{O}}{\overset{Q^1H}{\overset{|}{N}}}-C-N\overset{Q^8H}{\underset{Q^4H}{\diamond}} \quad \text{(mono-urea),}$$

or $R^2-\underset{\overset{\|}{O}}{\overset{Q^1H}{\overset{|}{N}}}-C-\underset{}{\overset{Q^1H}{\overset{|}{N}}}-R^2-N\underset{\underset{O}{\overset{\|}{C}}}{\overset{R^1}{\diamond}}N-Q^6H \quad \text{(bis-urea)}$ where $R^1$, $R^2$, $Q^1$, $Q^4$, $Q^6$ and $Q^8$ are as defined above.

The preferred ureas are unsubstituted, having the formula:

$$HN\underset{\underset{O}{\overset{\|}{C}}}{\overset{R^1}{\diamond}}N-Z^1$$

where $Z^1$ is $$R^2-NH-\underset{\overset{\|}{O}}{C}-NH_2 \quad \text{(mono-urea), or}$$

$$R^2-NH-\underset{\overset{\|}{O}}{C}-NH-R^2-N\underset{\underset{O}{\overset{\|}{C}}}{\overset{R^1}{\diamond}}NH \quad \text{(bis-urea),}$$

where $R^1$ is ethylene or propylene, preferably ethylene, and $R^2$ is an alkylene group having 2 to 10 carbon atoms, with 2 to 6 carbon atoms more preferred, and especially 2 to 4 carbon atoms.

It is presently preferred to use a bis-urea as the alkylene ureido alkyl urea reactant in practicing this invention. Suitable bis-ureas have the formula:

(BIS-V)
$$HQ^6-N\underset{\underset{O}{\overset{\|}{C}}}{\overset{R^1}{\diamond}}N-R^2-\underset{\overset{\|}{O}}{\overset{Q^1H}{\overset{|}{N}}}-C-\underset{}{\overset{Q^1H}{\overset{|}{N}}}-R^2-N\underset{\underset{O}{\overset{\|}{C}}}{\overset{R^1}{\diamond}}N-Q^6H$$

where $R^1$, $R^2$, $Q^1$ and $Q^6$ are as defined above. The preferred bis-ureas are unsubstituted, having the formula:

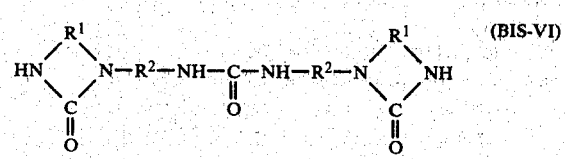

where $R^1$ is ethylene or propylene, preferably ethylene, and $R^2$ is an alkylene group having 2 to 10 carbon atoms, with 2 to 6 carbon atoms more preferred, and especially 2 to 4 carbon atoms.

Compounds of the formula Bis-VI are formed as co-products in the synthesis of the corresponding omega-amino alkylene urea. Thus, as disclosed in application Serial No. 157,238, compounds having the formula:

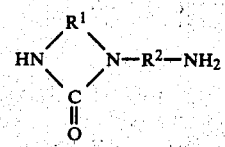

may be made by first reacting a dialkylene triamine, $H_2N-R^1-NHR^2-NH_2$, with urea,

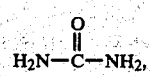

in the presence of heat to form

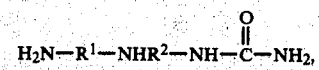

which when heated liberates ammonia and cyclizes to yield the omega-amino alkylene urea of formula VI. The bis-urea is formed along with the omega-amino alkylene urea, and by using an excess of urea, the yield of the bis-alkylene urea can be increased. In keeping with the concept of the invention, mixtures of the bis-urea and the co-produced omega-amino alkylene urea may be used as reactants with an unsaturated glycidyl ether or ester in the process of the present invention.

As disclosed in application Ser. No. 157,238, and indicated above, the preferred omega-amino alkylene urea is AEEU, which is the compound having the formula VI where both $R^1$ and $R^2$ are ethylene. AEEU can be made by the reaction of diethylene triamine and urea as described above, and a co-product of the reaction is the compound having the formula "bis-AEEU" given above, the preferred bis-urea of the present invention. An excess of urea is used to maximize the yield of "bis-AEEU".

The synthesis of AEEU and "bis-AEEU" are described in U.S. Pat. No. 2,613,212.

Substituted omega-amino alkylene ureas of formula V, including substituted derivatives of AEEU, may be formed by reacting an omega-amino alkylene urea of formula VI, such as AEEU, with one or more alkylene oxides having 2 to about 20, preferably 2 to about 6, most preferably 2 or 3, carbon atoms. For example, one mole of ethylene oxide,

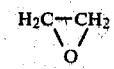

may be heated with one mole of AEEU to form:

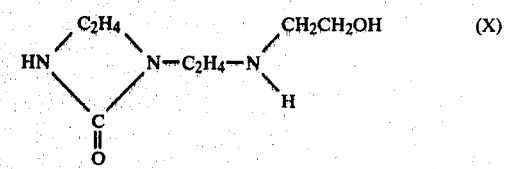

If a molar ratio of ethylene oxide to AEEU of 2:1 is used, the following substituted omega-amino alkylene urea is formed:

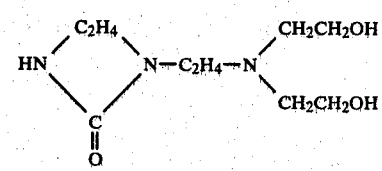

Subsequent moles of ethylene oxide would add to the ring nitrogen or to the hydroxyl moieties.

Similarly, if 1 mole and 2 moles, respectively, of propylene oxide,

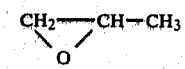

are reacted with AEEU, Structures XA and XIA would be two of the possible structures that would result:

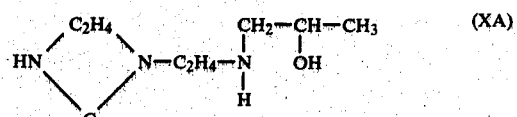

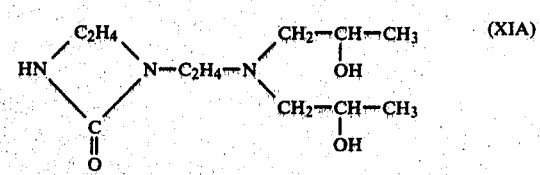

These alkoxylation techniques likewise may be used to form the substituted bis-ureas of formula BIS-VI, including substituted derivatives of the compound designated herein as "bis-AEEU". Included among contemplated alkoxylating agents are linear or branched alkylene oxides, such as ethylene oxide and propylene oxide, alkoxyalkylene oxides, such as butyl glycidyl ether, cycloalkylene oxides, such as cyclohexene oxide, cycloalkoxyalkylene oxides, such as cyclohexyl glycidyl ether, aryl oxides such as styrene oxide, and aryloxyalkylene oxides such as phenyl glycidyl ether. Mixtures of alkylene oxides may be used. The preferred alkoxylating agents are ethylene oxide, propylene oxide and mixtures thereof.

In general, the number of moles of alkylene oxide can be selected as desired, with from 1 to about 100 being contemplated, preferably 1 to about 75, more preferably 1 to about 20, and most preferably 1 to about 10. The temperature conditions are selected to optimize the progress of the reaction considering the particular alkoxylating agent, and it is generally desired to employ a catalyst, such as a Lewis acid or base. In general, process conditions, including temperatures and catalysts, as are known in the art in connection with alkoxylation reactions may be employed to produce substituted derivatives of "bis-AEEU" or other bis-ureas which in turn can be used as starting reactants for the monomers of this invention.

Mono-ureas useful in the practice of the present invention also may be formed by the reaction of a dialkylene triamine with urea. Suitable mono-ureas have the formula:

$$HQ^6-N\diagup^{R^1}\diagdown N-R^2-N(Q^1H)-C(=O)-N(Q^8H)(Q^4H) \quad \text{(MONO-V)}$$

where $R^1$, $R^2$, $Q^1$, $Q^4$, $Q^6$ and $Q^8$ are as defined above. The preferred mono-ureas are unsubstituted and have the formula:

$$HN\diagup^{R^1}\diagdown N-R^2-NH-C(=O)-NH_2 \quad \text{(MONO-VI)}$$

where $R^1$ is ethylene or propylene, preferably ethylene, and $R^2$ is an alkylene group having 2 to 10 carbon atoms, with 2 to 6 carbon atoms more preferred, and especially 2 to 4 carbon atoms. The most preferred mono-urea is that analogous to AEEU, i.e. where both $R^1$ and $R^2$ in formula MONO-VI are ethylene, which is the compound having the formula:

$$HN\diagup^{C_2H_4}\diagdown N-C_2H_4-NH-C(=O)-NH_2 \quad \text{("MONO-AEEU")}$$

Substituted mono-ureas of formula MONO-V, including substituted derivatives of the compound designated herein as "Mono-AEEU," may be prepared by using the same alkoxylation techniques as described above in connection with the alkoxylation of omega-amino alkylene ureas and the bis-ureas. Thus, the same alkoxylating agents and molar amounts as described above can be used to make the alkoxylated mono-ureas useful in the practice of this invention, and the processing conditions, such as temperatures and catalysts, are selected to optimize the progress of the reaction considering the particular alkoxylating agent as indicated above.

In keeping with the concept of the invention, mixtures of different mono-ureas may be used. Also mixtures of mono-ureas with the bis-ureas and/or omega-amino alkylene ureas may be used in practicing this invention.

In accordance with the process of the present invention, a mono-urea or bis-urea as described above is reacted with an unsaturated glycidyl ether or ester having the formula:

$$CH_2\underset{\diagdown O \diagup}{-}CH-CH_2-Q^3-O-Y-C(R^3)=CH(R^4) \quad \text{(VII)}$$

where $Q^3$, $Y$, $R^3$ and $R^4$ are as defined above. It is preferred to use unsaturated glycidyl ethers having the formula:

$$CH_2\underset{\diagdown O \diagup}{-}CH-CH_2-O-CH_2-C(R^3)=CH(R^4) \quad \text{(IX)}$$

where $R^3$ is H or $CH_3$, preferably H, and $R^4$ is H or $CH_3$, preferably H.

Compounds of the formula IX may be made by first reacting epichlorohydrin, $$CH_2\underset{\diagdown O \diagup}{-}CH-CH_2Cl,$$

with an allylic alcohol, $$CH(R^4)=C(R^3)-CH_2OH,$$

in the presence of a Lewis acid catalyst, such as $BF_3$ or $SnCl_4$, to produce the chlorohydrin:

$$CH_2(Cl)-CH(OH)-CH_2-O-CH_2-C(R^3)=CH(R^4) \quad \text{(XII)}$$

The chlorohydrin XII may then be reacted with base, such as NaOH, to eliminate HCl and close the ring thereby forming an unsaturated glycidyl ether having the formula IX. Among suitable starting allyic alcohols are allyl alcohol, $CH_2=CH-CH_2OH$, crotyl alcohol, $CH_3-CH=CH-CH_2OH$, and methallyl alcohol, $$CH_2=C(CH_3)-CH_2OH.$$

The most preferred unsaturated glycidyl ether for use in the production of the monomers of this invention is allyl glycidyl ether ("AGE"), which is the compound having the formula IX where both $R^3$ and $R^4$ are hydrogen:

$$CH_2\underset{\diagdown O \diagup}{-}CH-CH_2-O-CH_2-CH=CH_2 \text{ (AGE)}$$

AGE can be made by the reaction of allyl alcohol and epichlorohydrin as described above, and is available commercially.

Substituted glycidyl ethers of formula VII where Y is CH₂, including substituted derivatives of AGE, may be formed by reacting the starting allylic alcohol, such as allyl alcohol, with one or more alkylene oxides having 2 to about 20, preferably 2 to about 6, most preferably 2 to 3, carbon atoms. For example, one mole of ethylene oxide may be reacted with one mole of allyl alcohol in the presence of an acid or base, such as sodium methoxide, to from an ethoxylated allyl alcohol:

$$CH_2=CH-CH_2-O-CH_2-\overset{OH}{\underset{|}{CH_2}} \quad (XIII)$$

which then may be reacted with epichlorohydrin as described above. Subsequent moles of ethylene oxide would add to form a chain represented by the formula:

$$CH_2=CH-CH_2-O-CH_2-CH_2-O-_nH \quad (XIV)$$

where n is the number of moles. In general, the number of moles n of alkylene oxide can be selected as desired, with from 1 to about 100 being contemplated, preferably 1 to about 75, more preferably 1 to about 20, and most preferably 1 to about 10. Allyl alcohol can also be propoxylated with propylene oxide to yield structures analogous to XIII and XIV. The processing conditions, such as temperature and catalyst, are selected to optimize the progress of the reaction considering the particular alkoxylating agent, and in general may be chosen as known in the art in connection with alkoxylation of alcohols.

Included among contemplated alkoxylating agents are linear or branched alkylene oxides, alkoxyalkylene oxides, cycloalkylene oxides, cycloalkoxyalkylene oxides, arylalkylene oxides, and aryloxyalkylene oxides as described above in connection with the alkoxylation of omega-amino alkylene ureas. Mixtures of alkylene oxides may be used. The preferred alkoxylating agents are ethylene oxide, propylene oxide and mixtures thereof.

It is within the purview of the invention to employ an unsaturated glycidyl ester having the formula:

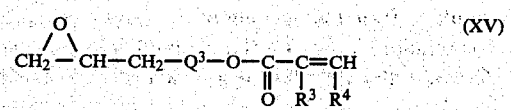
(XV)

where Q³, R³ and R⁴ are as defined above. It is preferred to use a glycidyl ester having the formula:

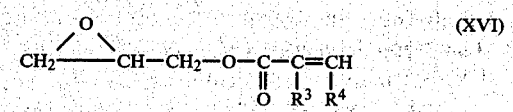
(XVI)

where R³ is H or CH₃ and R⁴ is H or CH₃, preferably H.

The most preferred unsaturated glycidyl esters are glycidyl methacrylate

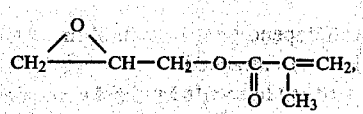

and glycidyl acrylate,

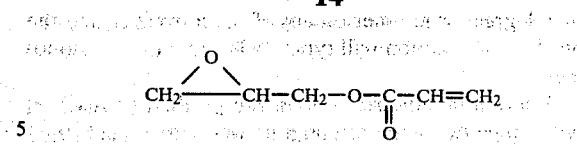

both of which are commercially available.

In accordance with the present invention, monomers useful as wet adhesion promoters in aqueous emulsion polymer systems are prepared by reacting an unsaturated glycidyl ether or ester having the formula:

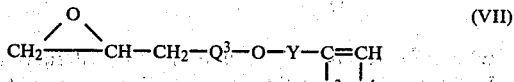
(VII)

with a urea having the formula:

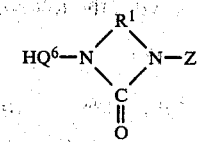

where R¹, Q⁶ and Z are defined above.

The molar ratio of the glycidyl ether or ester to urea may vary. Ranges of molar ratio include from about 0.5 to about 10 moles of glycidyl ether or ester per mole of urea, preferably about 0.5 to about 8, more preferably about 0.5 to about 6, moles of glycidyl ether or ester per mole of urea. It is most preferred to use a molar ratio of glycidyl ether or ester to urea of about 1:1 to about 4:1.

The reaction is best effected in the presence of a catalyst, such as an acid or base, and may be conducted over a wide temperature range. In general, a temperature and time period at least sufficient to effect the reaction are used. Effective temperatures may range from ambient temperature to about 500° C. Preferably, the temperature is from about 50° C. to about 250° C. The reaction time may be from about 1 to about 8 hours, preferably from about 2 to about 3 hours.

The most preferred embodiment of the process is the reaction of AGE with the compound designated above as "bis-AEEU" in a molar ratio of about 0.5 to about 10, preferably about 1 to about 6 and most preferably 1 to 4, moles of AGE per mole of bis-AEEU at a temperature of from about 50° C. to about 250° C., preferably about 100° C. to about 200° C., and most preferably about 120° C. to 150° C. in the presence of a metal alkoxide or aryloxide.

In the process of the present invention, the oxirane ring of the glycidyl ether or ester reacts at at least one of the available amino nitrogen sites to form either

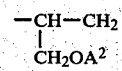

attached to the nitrogen or

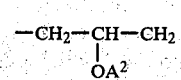

attached to the nitrogen, where A² is as defined above. It is believed that the attack occurs preferentially on a ring nitrogen, but statistically the attack will occur to one degree or another on any of the nitrogens, and the product of reaction will typically be a mixture of monomers.

Where a mono-urea is used, the product of reaction will typically comprise a mixture of compounds having the formula:

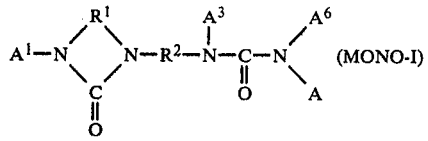

where $R^1$, $R^2$, A, $A^1$, $A^3$ and $A^6$ are as defined above. For example, when the compound designated above as "mono-AEEU" is reacted with AGE in accordance with this invention, the resultant product will usually be a mixture which includes the following compounds:

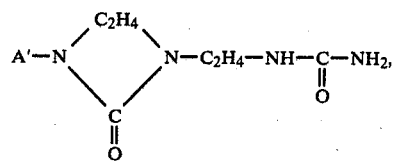

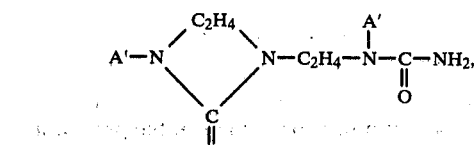

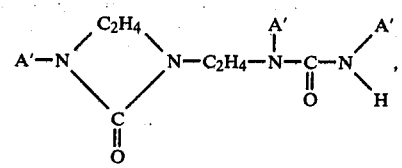

and

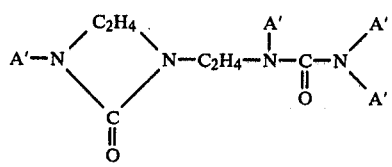

where A' is $-Q^2-O-CH_2-CH=CH_2$.

Where a bis-urea is used, the product of reaction will typically comprise a mixture of compounds having the formula:

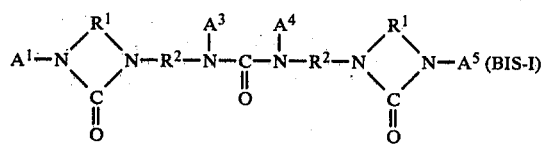

where $A^1$, $A^3$, $A^4$, $A^5$, $R^1$ and $R^2$ are as defined above. For example, where AGE is reacted with the compound designated above as "bis-AEEU" in accordance with the present invention, the reaction product will usually be a mixture which includes the following compounds:

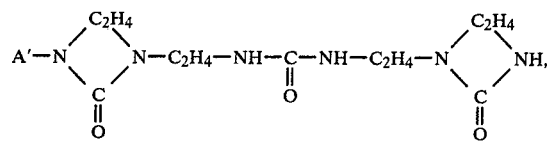

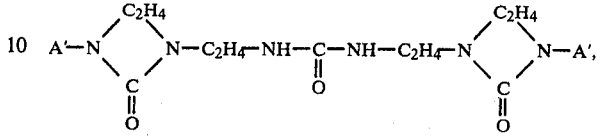

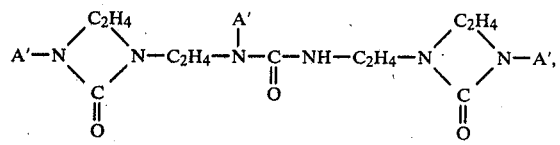

and

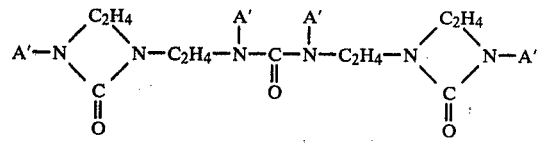

where A' is $-Q^2-O-CH_2-CH=CH_2$.

In the compounds of the present invention, as represented by the formulas MONO-I AND BIS-I, one or more of the "A" groups contains the moiety

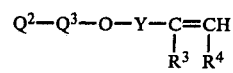

in which $Q^2$ is the hydroxyl-containing moiety $$\begin{array}{cc} CH-CH_2 & \text{or} \quad CH_2-CH-CH \\ | & \qquad\qquad | \\ CH_2OH & \qquad\qquad OH \end{array}$$

resulting from the opening of the oxirane ring, $Q^3$ is the substitution, if any, on the glycidyl ether or ester, Y is $CH_2$ if a glycidyl ether is used and

if a glycidyl ester is used, $R^3$ and $R^4$ are independently H or $CH_3$ as defined above in connection with the glycidyl ether or ester; and $R^1$ and $R^2$ are the alkylene groups as defined above. Which of the "A" groups have the

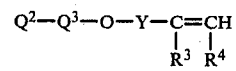

moieties will depend upon which of the available nitrogen sites is or are attacked.

It is possible to have the glycidyl ether or ester react further with the reaction product through the hydroxyl functionality on the $Q^2$ moiety, substituting either

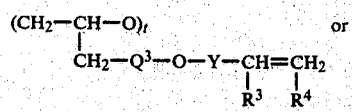

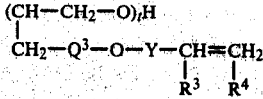

as defined above in connection with formula I, for the hydrogen. This further reaction may be accelerated by using an alkali metal alkoxide or aryloxide catalyst, such as sodium phenoxide, and a higher temperature.

In general, the more glycidyl ether or ester that is used relative to the amount of urea derivative defined herein, the more "poly-adduct," i.e. compound where more than one nitrogen is attacked, that is formed. Where the molar ratio of glycidyl ether or ester to urea derivative is less than 1 to 1, the formation of the "mono-adduct," i.e. where only one nitrogen is attacked, is favored.

In keeping with the inventive concept, the novel compounds produced by the reaction of an unsaturated glycidyl ether or ester with urea selected from the group consisting of a mono-(alkylene uredio alkyl) urea, a bis-(alkylene uredio alkyl) urea and mixtures thereof, are individually, a part of the invention herein. The novel compounds herein are selected from the group consisting of:

(BIS-I)

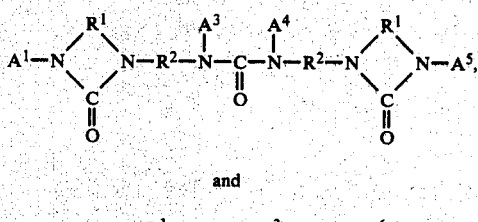

and (MONO-I)

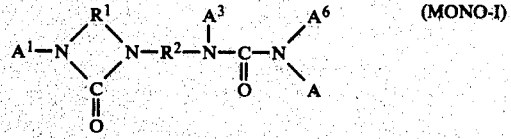

where A, $A^1$, $A^3$, $A^4$, $A^5$, $A^6$, $R^1$ and $R^2$ are as defined above.

Exemplary of compounds of the present invention are those having the formula BIS-I where $R^1$ is ethylene or propylene; $R^2$ is ethylene, propylene or butylene; at least one of $A^1$, $A^3$, $A^4$ and $A^5$ comprises the moiety

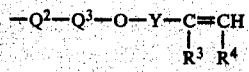

and preferably both $A^1$ and $A^5$ are

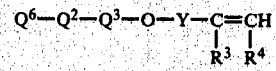

while $A^3$ and $A^4$ are independently H or the same as $A^1$ or $A^5$; $R^3$ is H or $CH_3$; $R^4$ is H or $CH_3$; $Q^6$ is $(C_2H_4\text{-}O)_r$ or $(C_3H_5\text{-}O)_r$ and r is zero or an integer from 1 to 20; $Q^2$ is

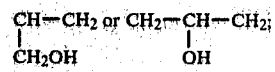

$Q^3$ is $(O\text{-}C_2H_4)_n$ or $(O\text{-}C_3H_5)_n$ and n is zero or an integer from 1 to 20; and Y is $CH_2$ or

A preferred group of compounds of the present invention consists of compounds having the formula BIS-I, where $R^1$ is ethylene or propylene; $R^2$ is ethylene, propylene, butylene, pentylene, hexylene, heptylene, octylene, nonylene or decylene; and any two of the four groups $A^1$, $A^3$, $A^4$ and $A^5$ are independently

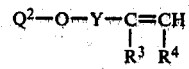

while the remaining two groups independently are H or

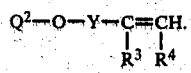

Exemplary of other compounds of the present invention are those having the formula MONO-I where $R^1$ is ethylene or propylene, $R^2$ is ethylene, propylene or butylene; at least one of A, $A^1$, $A^3$ and $A^6$ comprises the moiety

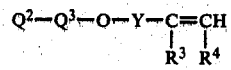

and preferably $A^1$ is

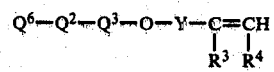

while A, $A^3$ and $A^6$ are independently H or the same as $A^1$; $R^3$ is H or $CH_3$; $R^4$ is H or $CH_3$; $Q^6$ is $(C_2H_4\text{-}O)_r$ or $(C_3H_5\text{-}O)_r$ and r is zero or an integer from 1 to 20; $Q^2$ is

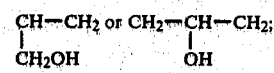

$Q^3$ is $(O\text{-}C_2H_4)_n$ or $(O\text{-}C_3H_5)_n$ or $(O\text{-}C_3H_5)_n$ and n is zero or an integer from 1 to 20; and Y is $CH_2$ or

A preferred group of compounds of the present invention derived from a mono-urea consists of compounds having the formula MONO-I where $R^1$ is ethylene or propylene; $R^2$ is ethylene, propylene, butylene, pentylene, hexylene, heptylene, octylene, nonylene or decylene; and any one of the four groups A, A¹, A³ and A⁶ is

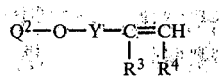

while the remaining three groups are independently H or

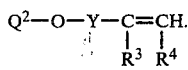

The reaction products and compounds of the present invention are polymerizable or copolymerizable through terminal unsaturation on the compounds. They may be used as comonomers in monomer systems for forming aqueous emulsion polymers, including in compositions comprising such monomers as methyl acrylate, ethyl acrylate, methyl methacrylate, butyl acrylate, 2-ethyl hexyl acrylate, other acrylates, methacrylates and their blends, styrene, vinyl toluene, vinyl acetate, vinyl esters of higher carboxylic acids than acetic acid, acrylonitrile, acrylamide, vinyl chloride and the like, and mixtures thereof.

In particular, the reaction products and compounds of this invention may be incorporated in effective amounts in aqueous polymer systems to enhance the wet adhesion of paints made from the polymers. The commonly used monomers in making acrylic paints are butyl acrylate, methyl methacrylate, ethyl acrylate and mixtures thereof. In acrylic paint compositions at least 50% of the polymer formed is comprised of an ester of acrylic or methacrylic acid. The vinyl-acrylic paints usually include vinyl acetate and butyl acrylate or 2-ethyl hexyl acrylate. In vinylacrylic paint compositions, at least 50% of the polymer formed is comprised of vinyl acetate, with the remainder being selected from the esters of acrylic or methacrylic acid.

The novel reaction products and compounds of this invention may be added to the monomer composition from which acrylic or vinyl-acrylic polymers are formed in a concentration which may vary over a wide range. Preferably, the concentration is at least sufficient to improve the wet adhesion of paints made from the polymer composition. Concentrations may range from about 0.1% to about 20% by weight based on the total weight of monomers. It is preferred that the concentration be from about 0.2% to about 5%.

In general, it has been found that effective amounts of the monomers of this invention to improve wet adhesion are higher for vinyl-acrylic paints than for acrylic paints. Thus, where a given concentration of monomer provides excellent wet adhesion for an acrylic paint, a higher concentration is often needed to produce similar results in a vinyl-acrylic composition. Effective, and optimum, concentrations are readily determinable following the procedures known in the art for evaluating wet adhesion of paints and the specific procedures described and illustrated herein.

The monomer composition may be used in conjunction with other ingredients, such as various free radical sources to initiate polymerization, surfactants with or without colloids to protect particles from agglomeration, and buffers to maintain a desired pH during polymerization, all as known in the art of polymerization, and the polymerization may be carried out using conditions and techniques as are known in the art. In addition to making emulsion polymers, it is contemplated that the reaction products and compounds of the present invention be used to form solution copolymers.

The invention will now be illustrated by the following examples. The examples are not intended to be limiting of the scope of the present invention. In conjunction with the general and detailed descriptions above, the examples provide further understanding of the present invention. In the examples, percentages are by weight.

EXAMPLE 1

A mixture of 284 parts of 1,3-bis-[2-(2-oxo-1-imidazolidinyl)ethyl]-urea ("bis-AEEU") and 10 g of sodium phenoxide was heated to 150° C. and 228 parts (2 molar equivalents) of allyl glycidyl ether (AGE) was added while the temperature was maintained at 150° C. by means of gentle heating. The product was isolated in essentially quantitative yield. The NMR spectrum of the product was consistent with a 2:1 adduct of AGE and "bis-AEEU".

EXAMPLE 2

A mixture of 284 parts of 1,3-bis-[2-(2-oxo-1-imidazolidinyl)ethyl]-urea("bis-AEEU") and 10 g of sodium phenoxide was heated to 150° C. and 456 parts (4 molar equivalents) of allyl glycidyl ether (AGE) was added while the temperature was maintained at 150° C. by means of gentle heating. The product was isolated in essentialy quantitative yield. The NMR spectrum of the product was consistent with a 4:1 adduct of AGE and "bis-AEEU".

To illustrate the use of the monomers of this invention as wet adhesion promoters, and to compare them with other monomers, various emulsion polymer systems or latexes were prepared as described below. Then, semi-gloss paints were prepared from the emulsion polymers by first obtaining a pigment dispersion of:

| Materials | Weight in grams |
|---|---|
| Water | 460 |
| Magnesium aluminum silicate (Bentone LT) | 16 |
| Antifoamer (Nopco NXZ) (proprietary composition-non ionic yellow amber liquid) | 4 |
| Dispersant (Potassium Tripolyphosphate - 20%) | 20 |
| Dispersant (Tamol 850 - sodium salt of a polymeric carboxylic acid) | 20 |
| Wetting agent (Triton CF-10-alkylaryl polyether) | 10 |
| Wet Edge Agent (Ethylene glycol) | 300 |
| Titanium dioxide (Titanox 2020) | 1100 |
| | 1930 |

These ingredients were mixed in high speed dispersing equipment until smooth. Then 160 g of the pigment dispersion was mixed with 179.5 g latex, 12.25 g ethylene glycol, 0.34 g antifoamer (Nopco NXZ), and 5.12 g Texanol (3-hydroxy isooctyl isobutyrate) using vigorous agitation.

The paints were evaluated for wet scrub properties using a modified ASTM-D 2486-69 Latex Paint Scrub Test. The test involved a 3 mil drawdown of high gloss, oil-based, enamel made on the full length of a Leneta Chart and air-dried seven days at room temperature. Next, simultaneous drawdowns of a control paint and the paint being evaluated across the gloss enamel near the center of the chart were made before air-drying for two days at room temperature.

The Leneta Chart was fastened to the glass base plate and mounted in the Gardner scrub tester. The scrub brush was soaked in a 2 percent solution of Triton X-100 (octyl phenoxy polyethoxy ethanol) for 30 minutes, then shaken vigorously to remove excess detergent solution. Ten grams of a scrub medium (well mixed 497 g water, 10 g cellosize WP-4400 hydroxy ethyl cellulose, 20 g Triton X-100, 20 g Trisodium Phosphate, 450 g #22 Silica and 2 g Acetic Acid) were spread evenly over the brush bristles. The brush was mounted in the holder of the Gardner scrub tester and the panel was wetted with 5 g water before beginning test. After each 250 cycles, before failure, 10 g scrub media was added, the brush was remounted and 5 g additional water was placed on the chart in the path of the brush before continuing the test.

In the following Examples 3 and 4, the reaction product obtained in Examples 1 and 2 were used in acrylic latex emulsions. The acrylic latex emulsions used were systems in which at least 50 percent of the polymer formed is comprised of an ester of acrylic or methacrylic acid. The emulsions were used in the semi-gloss paint formulation described above and evaluated for wet scrub properties.

EXAMPLE 3

An acrylic emulsion polymer, for paint application, containing 1 percent of the product obtained in Example 1 was prepared using the following procedure:

| Materials | Weight in grams |
|---|---|
| Butyl acrylate | 255 |
| Methyl Methacrylate | 240 |
| Product of Example 1 | 5 |
| Blend of sodium fatty alcohol polyether sulfate and octyl phenoxypoly(oxyethylene) ethanol surfactant at 42% solids | 39.7 |
| Sodium persulfate | 1.8 |
| Sodium metabisulfite | 1.5 |
| Water, deionized | 450 |
| | 993 |

Solutions of 1.8 g sodium persulfate in 36 g water and of 1.5 g sodium metabisulfite in 60 g water were prepared. There was then prepared a pre-emulsion of 150 g water, surfactant blend, butyl acrylate, and methacrylate. A one liter resin reactor was charged with 204 g water and product of Example 1. The reactor was purged with nitrogen and heated to 60° C. After the reactor reached 60° C., there was added 18 ml of the persulfate and 8 ml of metabisulfite solution, followed by addition of one percent of the pre-emulsion. After allowing seed latex formation for about 10 minutes, the pre-emulsion was added over a 2 to 2.5 hour period and the persulfate-metabisulfite solutions over 2.5 to 3 hours while holding the reactor temperature between 60°–65° C. The total polymerization time was approximately 3.5 hours. The latex was cooled and filtered. The latex was adjusted to 46% solids and a pH of 9.5 with ammonium hydroxide.

The emulsion polymer was used in the semi-gloss paint formulation that included titanium dioxide pigment. When the paint was subjected to the wet scrub test described above, no failure occurred by 1500 cycles indicating that the paint has excellent wet scrub properties.

EXAMPLE 4

An emulsion polymer was prepared in a manner similar to that in Example 3 with a monomer system containing 1.5 percent product of Example 2, 51 percent butyl acrylate and 47.5 percent methyl methacrylate. The emulsion polymer was used in the semi-gloss paint formulation. No failure occurred in the wet scrub test by 1500 cycles indicating that the paint has excellent wet scrub properties.

In the following Example 5, the reaction product obtained in Example 1 was used in vinyl acrylic emulsion. The vinyl acrylic emulsion used was a polymerizing system in which at least 50 percent of the monomer composition is vinyl acetate, the remainder being selected from the esters of acrylic or methaacrylic acid. Again, the emulsion was tested for wet scrub properties using the test set forth above.

EXAMPLE 5

A vinyl acrylic emulsion polymer, for paint application, containing 1.5 percent of the product obtained in Example 1 was prepared using the following procedure:

| Materials | Weight in grams |
|---|---|
| Vinyl acetate | 428.2 |
| Butyl acrylate | 119.5 |
| Product of Example 1 | 8.3 |
| Blend of sodium fatty alcohol poly(oxyethylene) sulfate and octyl phenoxypoly(oxyethylene) ethanol surfactant at 46 percent solids | 58.9 |
| Sodium carbonate | 1.5 |
| Hydroxyethyl ether of cellulose (Natrosol 180 LR) | 0.56 |
| Ammonium persulfate | 3.89 |
| Sodium metabisulfite | 3.33 |
| Water, deionized | 375.4 |
| | 999.58 |

A one liter reactor was charged with 264.2 g water, 5.8 g surfactant, and the hydroxyethyl cellulose. The reactor was purged with nitrogen and heated to 70° C. A solution of sodium metabisulfite, 53 g surfactant and 55.6 g water was prepared. After 8 ml of solution was removed, for initiation, the product of Example 1 was mixed into the solution. A solution of ammonium persulfate, sodium carbonate and 55.6 g water was prepared. The vinyl acetate and butyl acrylate were blended together. The 8 ml of metabisulfite solution, without the product of Example 1, was added to the reactor at 70° C. together with 5.5 ml of the ammonium persulfate solution and the monomer blend was then added dropwise. The monomer blend was added over a period of 4 hours. The metabisulfite solution was added over 4 hours and the persulfate solution over 4.5 hours. The total polymerization time was 5 hours for the run. The latex product was cooled and then filtered. The solids were adjusted to 46% and the pH raised to 9.5 with ammonium hydroxide.

The emulsion polymer was used in the semi-gloss paint formulation described above. No failure occurred in the wet scrub test by 1500 cycles indicating that the paint has excellent wet scrub properties.

In addition to the Examples given above, reference is made to the Examples set forth in related application Ser. No. 157,238, expressly incorporated by reference herein, which illustrate the performance of many other monomers as wet adhesion promoters.

The scope of the present invention is not limited by the description and Examples herein, and modifications can be made without departing from the spirit of the invention. For example, the reaction products and compounds of this invention may be used in coating compositions other than latex paints, such as paper coatings, printing inks, textile sizing agents, binders and the like. Moreover, modifications could be made in the structures of the compounds of this invention without affecting the essence of the invention.

What is claimed is:

1. A compound having the formula:

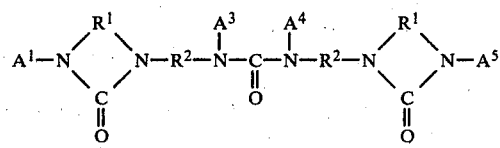

where $A^1$ and $A^5$ are each independently H, $Q^6H$ or

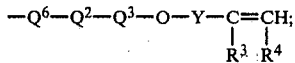

$A^3$ and $A^4$ are each independently H, $Q^1H$ or

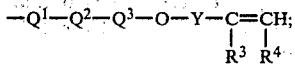

provided that at least one of $A^1$, $A^3$, $A^4$ and $A^5$ is a group having the moiety

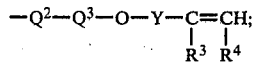

$R^1$ is alkylene having 2 to 3 carbon atoms;
$R^2$ is alkylene having 2 to about 10 carbon atoms;
$R^3$ is H or $CH_3$;
$R^4$ is H or $CH_3$ and may be the same as or different from $R^3$;
$Q^1$ is $(R^5\text{-}O)_m$ where m is zero or an integer from 1 to about 100, and $R^5$ is a linear or branched alkylene, alkoxyalkylene, cycloalkylene, cycloalkoxyalkylene, arylalkylene, or aryloxyalkylene residue having 2 to about 20 carbon atoms;
$Q^2$ is

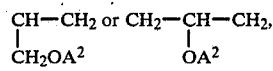

where $A^2$ is H,

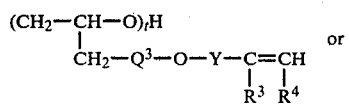

or

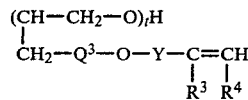

where t is zero or an integer from 1 to 10;
$Q^3$ is $(O\text{-}R^6)_n$ where n is zero or an integer from 1 to about 100 and may be the same as or different from m, and $R^6$ is a linear or branched alkylene, alkoxyalkylene, cycloalkylene, cycloalkoxyalkylene, arylalkylene or aryloxyalkylene residue having 2 to about 20 carbon atoms, and may be the same as or different from $R^5$;
$Q^6$ is $(R^9\text{-}O)_r$ where r is zero or an integer from 1 to about 100 and may be the same as or different from m and n and $R^9$ is a linear or branched alkylene, alkoxyalkylene, cycloalkylene, cycloalkoxyalkylene, arylalkylene, or aryloxyalkylene residue having 2 to about 20 carbon atoms, and may be the same as or different from $R^5$ and $R^6$; and
Y is $CH_2$ or

2. A compound according to claim 1 wherein $A^1$, $A^3$, $A^4$ and $A^5$ are each independently H or

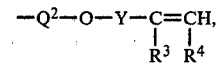

provided that at least one of $A^1$, $A^3$, $A^4$ and $A^5$ is

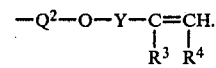

3. A compound according to claim 2 wherein $Q^2$ is

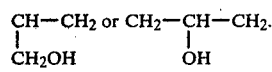

4. A compound according to claim 2 wherein Y is $CH_2$.

5. A compound according to claim 2 wherein Y is

6. A compound according to claim 2 wherein both $R^1$ and $R^2$ are ethylene.

7. A compound having the formula:

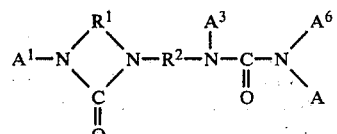

where
A is H, $Q^4H$ or

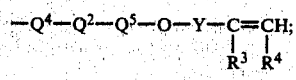

$A^1$ is H, $Q^6$H or

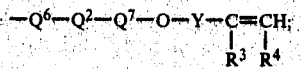

$A^3$ is H, $Q^1$H or

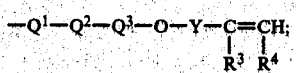

$A^6$ is H, $Q^8$H or

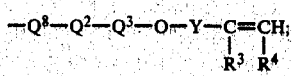

provided that at least one of A, $A^1$, $A^3$ or $A^6$ is a group having the moiety

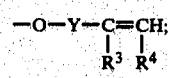

$R^1$ is alkylene having 2 to 3 carbon atoms;
$R^2$ is alkylene having 2 to about 10 carbon atoms;
$R^3$ is H or $CH_3$;
$R^4$ is H or $CH_3$ and may be the same as or different from $R^3$;
$Q^1$ is $(R^5\text{-O})_m$ where m is zero or an integer from 1 to about 100, and $R^5$ is a linear or branched alkylene, alkoxyalkylene, cycloalkylene, cycloalkoxyalkylene, arylalkylene, or aryloxyalkylene residue having 2 to about 20 carbon atoms;
$Q^2$ is

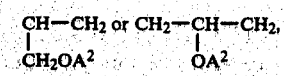

where $A^2$ is H,

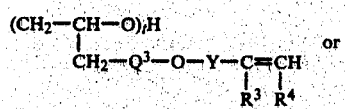

or

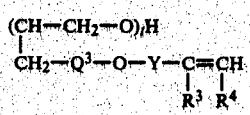

where t is zero or an integer from 1 to 10;
$Q^3$ is $(O\text{-}R^6)_n$ wherein n is zero or an integer from 1 to about 100 and may be the same as or different from m, and $R^6$ is a linear or branched alkylene, alkoxyalkylene, cycloalkylene, cycloalkoxyalkylene, arylalkylene or aryloxyalkylene residue having 2 to about 20 carbon atoms, and may be the same as or different from $R^5$;
$Q^4$ is $(R^7\text{-O})_p$ where p is zero or an integer from 1 to about 100 and may be the same as or different from m and n, and $R^7$ is a linear or branched alkylene, alkoxyalkylene, cycloalkylene, cycloalkoxyalkylene, arylalkylene, or aryloxyalkylene residue having 2 to about 20 carbon atoms, and may be the same as or different from $R^5$ or $R^6$;
$Q^5$ is $(O\text{-}R^8)_q$ where q is zero or an integer from 1 to about 100 and may be the same as or different from m, n and p, and $R^8$ is a linear or branched alkylene, alkoxyalkylene, cycloalkylene, cycloalkoxyalkylene, arylalkylene, or aryloxyalkylene residue having 2 to about 20 carbon atoms, and may be the same as or different from $R^5$, $R^6$ and $R^7$; and
$Q^6$ is $(R^9\text{-}O)_r$ where r is zero or an integer from 1 to about 100 and may be the same as or different from m, n, p and q, and $R^9$ is a linear or branched alkylene, alkoxyalkylene, cycloalkylene, cycloalkoxyalkylene, arylalkylene, or aryloxyalkylene residue having 2 to about 20 carbon atoms, and may be the same as or different from $R^5$, $R^6$, $R^7$ and $R^8$; and
$Q^7$ is $(O\text{-}R^{10})_s$ where s is zero or an integer from 1 to about 100 and may be the same as or different from m, n, p, q and r, and $R^{10}$ is a linear or branched alkylene, alkoxyalkylene, cycloalkylene, cycloalkoxyalkylene, arylalkylene or aryloxyalkylene residue having 2 to about 20 carbon atoms, and may be the same as or different from $R^5$, $R^6$, $R^7$, $R^8$, and $R^9$;
$Q^8$ is $(R^{11}\text{-}O)_w$ where w is zero or an integer from 1 to about 100 and may be the same as or different from m, n, p, q, r and s, and $R^{11}$ is a linear or branched alkylene, alkoxyalkylene, cycloalkylene, cycloalkoxyalkylene, arylalkylene or aryloxyalkylene residue having 2 to about 20 carbon atoms and may be the same as or different from $R^5$, $R^6$, $R^7$, $R^8$, $R^9$, and $R^{10}$; and
Y is $CH_2$ or

8. A compound according to claim 7 wherein A, $A^1$, and $A^3$ and $A^6$ are each independently H or

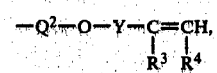

provided that at least one of A, $A^1$, $A^3$ and $A^6$ is

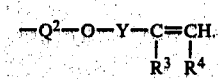

9. A compound according to claim 8 wherein $Q^2$ is

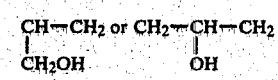

10. A compound according to claim 8 wherein Y is $CH_2$.

11. A compound according to claim 8 wherein Y is

12. A compound according to claim 8 wherein both $R^1$ and $R^2$ are ethylene.

13. A composition of matter made by reacting (1) an unsaturated glycidyl ether or ester having the formula:

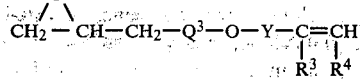

where
$R^3$ is H or $CH_3$;
$R^4$ is H or $CH_3$ and may be the same as or different from $R^3$;
Y is $CH_2$ or $$-\underset{\underset{O}{\|}}{C}-;$$

and
$Q^3$ is $(O-R^6)_n$ where n is zero or an integer from 1 to about 100 and $R^6$ is a linear or branched alkylene, alkoxyalkylene, cycloalkylene, cycloalkoxyalkylene, arylalkylene or aryloxyalkylene residue having 2 to about 20 carbon atoms, with (2) an alkylene urea having the formula:

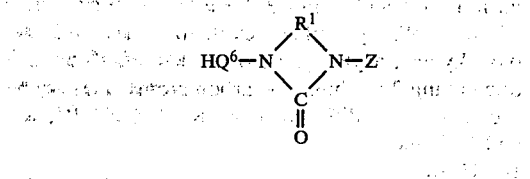

where Z is

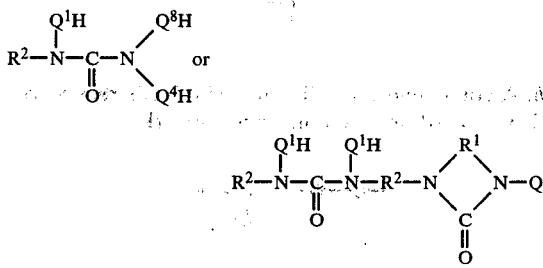

where
$R^1$ is alkylene having 2 to 3 carbon atoms;
$R^2$ is alkylene having 2 to about 10 carbon atoms;
$Q^1$ is $(R^5-O)_m$ where m is zero or an integer from 1 to about 100 and $R^5$ is a linear or branched alkylene, alkoxyalkylene, cycloalkylene, cycloalkoxyalkylene, arylalkylene or aryloxyalkylene residue having 2 to about 20 carbon atoms;
$Q^4$ is $(R^7-O)_p$ where p is zero or an integer from 1 to about 100 and may be the same as or different from m, and $R^7$ is a linear or branched alkylene, alkox- yalkylene, cycloalkylene, cycloalkoxyalkylene, arylalkylene, or aryloxyalkylene residue having 2 to about 20 carbon atoms, and may be the same as or different from $R^5$;
$Q^6$ is $(R^9-O)_r$ where r is zero or an integer from 1 to about 100 and may be the same as or different from m and p, and $R^9$ is a linear or branched alkylene, alkoxyalkylene, cycloalkylene, cycloalkoxyalkylene, arylalkylene, or aryloxyalkylene residue having 2 to about 20 carbon atoms, and may be the same as or different from $R^5$ and $R^7$; and
$Q^8$ is $(R^{11}-O)_w$ where w is zero or an integer from 1 to about 100 and may be the same as or different from m, p and r, and $R^{11}$ is a linear or branched alkylene, alkoxyalkylene, cycloalkylene, cycloalkoxyalkylene, arylalkylene or aryloxyalkylene residue having 2 to about 20 carbon atoms and may be the same as or different from $R^5$, $R^7$ and $R^9$; and in a molar ratio of from about 0.5 to about 10 moles of unsaturated glycidyl ether or ester per mole of alkylene urea and at a temperature in the range of from about 50° C. to about 250° C.

14. A composition of matter according to claim 13 wherein the unsaturated glycidyl ether or ester is an ether having the formula:

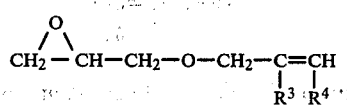

where $R^3$ is H or $CH_3$; and $R^4$ is H or $CH_3$.

15. A composition of matter according to claim 13 wherein the alkylene urea has the formula:

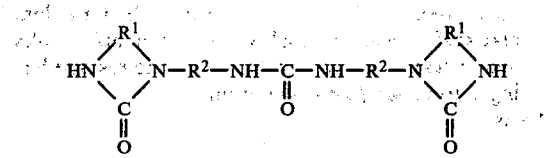

where $R^1$ is alkylene having 2 to 3 carbon atoms; and $R^2$ is alkylene having 2 to about 10 carbon atoms.

16. A composition of matter according to claim 15 wherein the unsaturated glycidyl ether or ester is allyl glycidyl ether.

17. A composition of matter according to claim 13 wherein the alkylene urea has the formula:

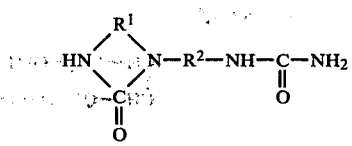

where $R^1$ is alkylene having 2 to 3 carbon atoms and $R^2$ is alkylene having 2 to about 10 carbon atoms.

* * * * *